US00PP37406P2

(12) United States Plant Patent
Wismans

(10) Patent No.: US PP37,406 P2
(45) Date of Patent: May 5, 2026

(54) ***HELICONIA* PLANT NAMED 'LOVE BIRD'**

(50) Latin Name: *Heliconia psittacorum*
Varietal Denomination: LOVE BIRD

(71) Applicant: Lucanne B.V., Haalderen (NL)

(72) Inventor: Peter Wismans, Haalderen (NL)

(73) Assignee: Lucanne B.V. (NL)

( * ) Notice: Subject to any disclaimer, the term of this patent is extended or adjusted under 35 U.S.C. 154(b) by 0 days.

(21) Appl. No.: 19/289,750

(22) Filed: Aug. 4, 2025

(51) Int. Cl.
*A01H 5/02* (2018.01)
*A01H 6/00* (2018.01)

(52) U.S. Cl.
USPC ..... Plt./263.1

(58) Field of Classification Search
USPC ..... Plt./263.1
See application file for complete search history.

*Primary Examiner* — Susan McCormick Ewoldt
*Assistant Examiner* — Zachariah Allan Kay

(57) ABSTRACT

A new and distinct cultivar of *Heliconia* plant named 'LOVE BIRD' is disclosed, characterized by dark foliage color, and bright orange flower color. Plants are compact, freely-branching, and are flowering and market ready in 100 days from planting a rooted cutting. The new variety is a *Heliconia*, typically produced as an outdoor ornamental plant.

2 Drawing Sheets

Latin name of the genus and species: *Heliconia psittacorum.*

Cultivar denomination: 'LOVE BIRD'.

BACKGROUND OF THE INVENTION

The new *Heliconia* cultivar is a product of a planned breeding program conducted by the inventor at a nursery in De Lier, The Netherlands. The objective of the breeding program was to breed more compact and responsive *Heliconia* cultivars. The cross resulting in this new cultivar was made during August of 2016.

The seed parent is the unpatented *Heliconia* cultivar 'KR463'. The pollen parent is the unpatented cultivar *Heliconia* 'KR443'. The new cultivar was discovered in August of 2021 by the inventor at the same location in De Lier, The Netherlands.

Asexual reproduction of the new cultivar was performed by tissue cuttings in January of 2022 at the same nursery in De Lier, The Netherlands, and has shown that the unique features of this cultivar are stable and reproduced true to type in successive generations.

SUMMARY OF THE INVENTION

The cultivar 'LOVE BIRD' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'LOVE BIRD' These characteristics in combination distinguish 'LOVE BIRD' as a new and distinct *Heliconia* cultivar:

1. A flowering market ready plant can be produced in about 100 days at 25° C. This is at least 2 weeks faster than typical for similar varieties in the market.
2. Bright flower color.
3. Dark foliage.

4. Freely branching with basal branches.
5. Compact growth habit.

Records of the breeding history contain the names of the parent varieties, but, characteristics are not available. The inventor cannot make a comparison to either of the parent varieties as the information is no longer available.

COMMERCIAL COMPARISON

Plants of the new cultivar 'LOVE BIRD' can be compared to the unpatented commercial cultivar *Heliconia* 'Ruby Parrot'. These cultivars are similar in most horticultural characteristics, however 'LOVE BIRD' differs in the following:

1. Flower color of the new cultivar is orange, while the flower color of this comparator is yellow.
2. Plants of the new cultivar are flowering and market ready 2 weeks earlier than plants of this comparator.
3. Foliage color of the new cultivar is darker than the foliage color of this comparator.

BRIEF DESCRIPTION OF THE PHOTOGRAPHS

Figure 1:
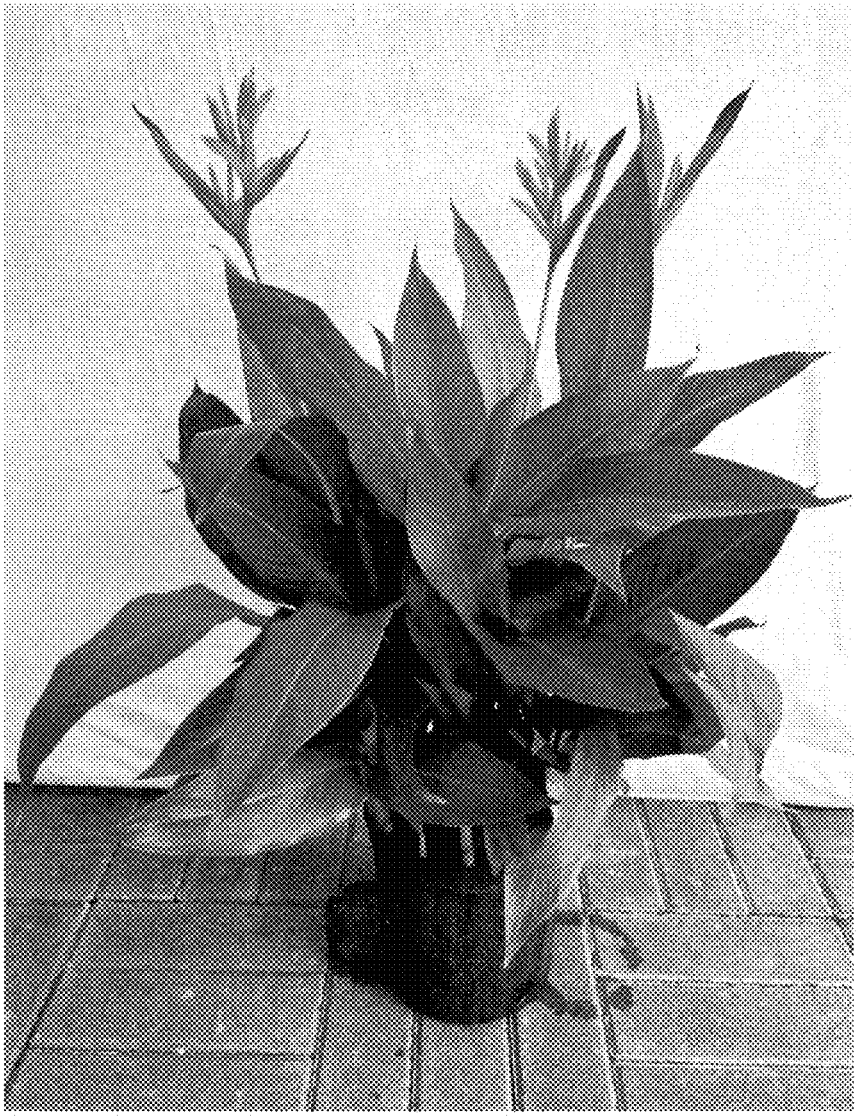

The accompanying photograph in FIG. 1 illustrates in full color a typical plant of 'LOVE BIRD'. Age of the plant photographed is approximately 1.5 years.

Figure 2:
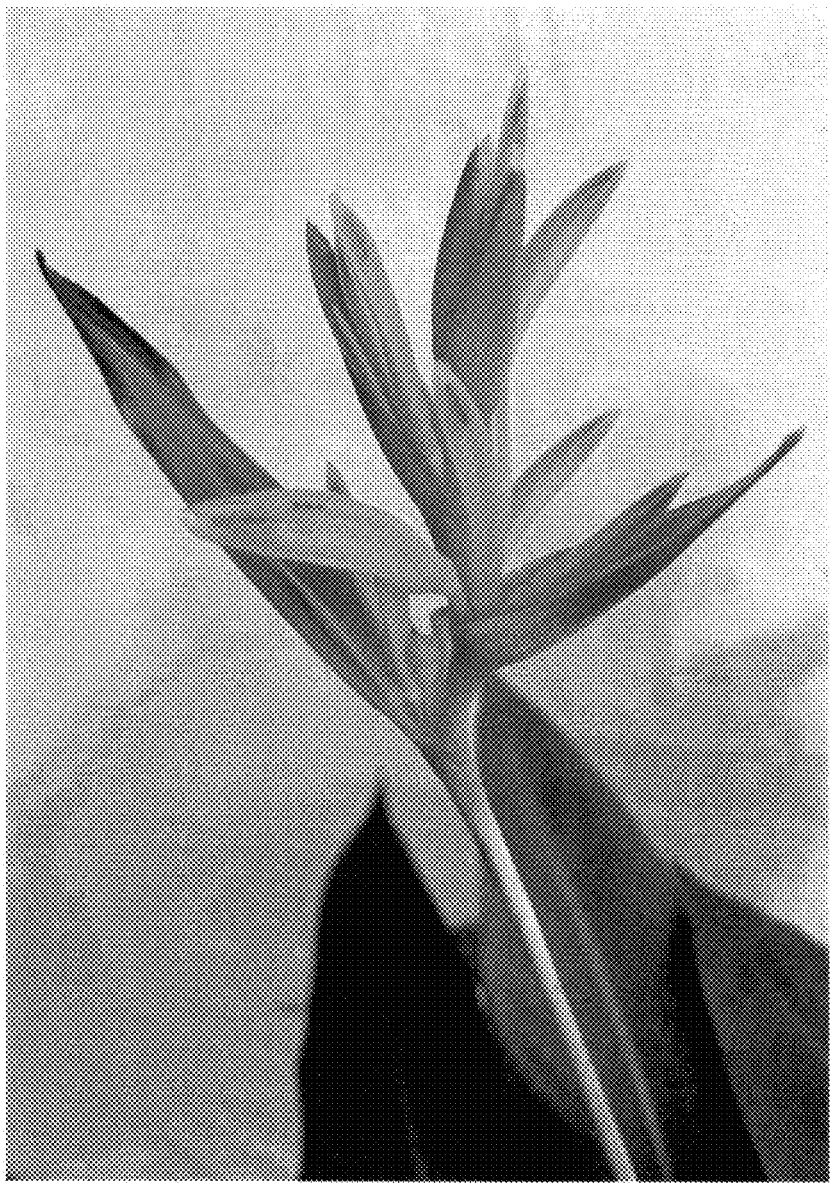

FIG. 2 illustrates a close-up view of a typical flower.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 1996, except where general terms of ordinary dictionary significance are used. The following observations and measurements describe 'LOVE BIRD' plants grown in a shade house in Key Largo, Florida. The growing temperature ranged from approximately 15° C. to 35° C. during the day and from approximately 15° C. to 20° C. during the night. General light conditions are bright, normal sunlight. Measurements and numerical values represent averages of typical plant types.

Botanical classification: *Heliconia psittacorum* 'LOVE BIRD'.

PROPAGATION

Time to initiate roots: 10 days at approximately 22° C.

Time to produce a rooted cutting: 42 days at approximately 22° C.

Time to produce a finished plant: 100 days at 25° C. from a rooted tissue culture young plant.

Rooting habit and description: Clear white, thick roots with fleshy texture.

PLANT

Age of plant described: Approximately 14 weeks.

Growth habit: Upright.

Height: 70 cm to top of floral plane; 38 cm to top of foliar plane.

Spread: 47 cm.

Branching characteristics: Free, basal branching.

Diameter of basal branches: 2.8 cm.

Length of basal branches: 36 cm.

Quantity of basal branches: Average 12.

Basal branch strength: Strong, not lodging over or easily broken.

Stem color: RHS Yellow-Green 143A flushed Greyed-Red 181A.

Stem shape: Ovate.

Stem pubescence: None.

FOLIAGE

Leaf:
- *Arrangement*.—Alternate, single.
- *Quantity*.—Approximately 6 per stem.
- *Average length*.—28 to 34 cm.
- *Average width*.—8 to 10 cm.

Leaflet:
- *Quantity*.—Approximately 5 to 7 per leaf.
- *Average length*.—28 to 34 cm.
- *Average width*.—8 to 10 cm.
- *Shape of blade*.—Lanceolate.
- *Apex*.—Apiculate.
- *Base*.—Oblique.
- *Margin*.—Entire.
- *Texture of top surface*.—Glabrous, glossy.
- *Texture of bottom surface*.—Glabrous, glossy.
- *Color*.—Young foliage upper side: RHS Green 137C. Young foliage under side: RHS Green 137C. Mature foliage upper side: RHS Green 137A. Mature foliage under side: RHS Green 137B.
- *Venation*.—Type: Pinnate. Venation color upper side: RHS Green 138B. Venation color under side: RHS Green 138C.

Petiole:
- *Average length*.—2 cm.
- *Average diameter*.—0.4 cm.
- *Color*.—RHS Green 138B.
- *Texture*.—Glabrous, glossy.

FLOWER

Natural flowering season: Year-round in Florida, US.

Longevity: 14 days.

Fragrance: None.

Flower type: Single.

Flower size:
- *Height*.—14 cm.
- *Diameter*.—13 cm.

Pedicel:
- *Length*.—1.5 to 2 cm.
- *Diameter*.—3 cm.
- *Angle*.—20°.
- *Strength*.—Strong, not easily broken.
- *Color*.—RHS Orange 25B.

Petals:
- *Number*.—3 per flower.
- *Length*.—4.5 cm.
- *Width*.—7 mm.
- *Shape*.—Narrow lanceolate.
- *Margin*.—Entire.
- *Apex*.—Acute.
- *Base*.—
- *Texture*.—Both sides glabrous.
- *Color*.—Young, upper surface: RHS Orange 25C. Young, lower surface: RHS Orange 25D. Mature, upper surface: RHS Orange 25B. Mature, lower surface: RHS Orange 25C.

Bud:
- *Shape*.—Narrow lanceolate.
- *Length*.—10 cm.
- *Diameter*.—9 mm.
- *Color*.—RHS Orange 25C.

Sepals:
- *Number*.—3 per flower.
- *Length*.—8 cm.
- *Width*.—9 cm.
- *Shape*.—Narrow lanceolate.
- *Apex*.—Long acuminate.
- *Color*.—Young, upper surface: RHS Red-Orange 43B. Young, lower surface: RHS Red-Orange 44B. Mature, upper surface: RHS Red-Orange 34A. Mature, lower surface: RHS Red-Orange 44A.
- *Texture*.—Glabrous, shiny, and glossy.
- *Margin*.—Entire.

Calyx:
- *Length*.—4.5 cm.
- *Width*.—7 mm.
- *Shape*.—Tubular.

Peduncle:
- *Length*.—20 cm.
- *Width*.—4 mm.
- *Aspect*.—Rigid.
- *Angle*.—0°.

*Shape*.—Upright.
*Texture*.—Smooth.
*Color*.—RHS Yellow-Green 144A.
*Strength*.—Strong, not easily broken.

REPRODUCTIVE ORGANS

Stamens:
*Number*.—Average 6.
*Length*.—5 cm.
*Width*.—6 mm.
Anthers:
*Length*.—7 mm.
*Width*.—1 mm.
*Color*.—Edge and center RHS Orange 23D.
*Pollen*.—None observed.
Pistil:
*Number*.—Approximately 10-15.
*Pistil length*.—Approximately 4 mm.
*Style*.—Length: 5 mm. Color: RHS Orange 23D.
*Stigma*.—Shape: Three-lobed. Color: RHS Orange 22B.
*Ovary*.—Length: 3 mm. Color: RHS Orange 24A, with and without seed.

OTHER CHARACTERISTICS

Seeds and fruits: Not observed.
Disease/pest resistance: Neither resistance nor susceptibility to the normal diseases and pests of *Heliconia* has been observed.

What is claimed is:

1. A new and distinct cultivar of *Heliconia* plant named 'LOVE BIRD' as herein illustrated and described.

* * * * *